(12) United States Patent
Minakata et al.

(10) Patent No.: US 7,371,810 B1
(45) Date of Patent: May 13, 2008

(54) TACHYKININ PEPTIDES, PRECURSOR PEPTIDES THEREOF AND GENES ENCODING THE SAME

(75) Inventors: Hiroyuki Minakata, Kawabe-gun (JP); Eiko Iwakoshi, Kashiwara (JP); Kyoko Kuroda, Kyoto (JP)

(73) Assignee: Suntory Limited, Oshaka-shi (JP)

( * ) Notice: Subject to any disclaimer, the term of this patent is extended or adjusted under 35 U.S.C. 154(b) by 0 days.

(21) Appl. No.: 10/048,401

(22) PCT Filed: Jul. 25, 2000

(86) PCT No.: PCT/JP00/04944

§ 371 (c)(1),
(2), (4) Date: May 11, 2005

(87) PCT Pub. No.: WO01/09171

PCT Pub. Date: Feb. 8, 2001

(30) Foreign Application Priority Data

Jul. 30, 1999 (JP) .................................. 11-216922
Mar. 27, 2000 (JP) ............................. 2000-086236

(51) Int. Cl.
*A61K 38/00* (2006.01)
(52) U.S. Cl. ........................................ 530/300; 530/314
(58) Field of Classification Search ..................... None
See application file for complete search history.

(56) References Cited

OTHER PUBLICATIONS

Norinder et al., J. Peptide Res., 1997, 49: 155-162.*
Ngo et al., in The Protein Folding Problem and Tertiary Structure Prediction, 1994, Merz et al. (ed.), Birkhauser, Boston, MA, pp. 433 and 492-495.*
Tim Badgery-Parker et al., "Receptor Binding Profile of Neuropeptide γ and Its Fragments: Comparison with the Nonmammalian Peptides Carassin and Ranakinin at Three Mammalian Tachykinin Receptors", Peptides, 1993, pp. 771-775, vol. 14, USA, XP002287463.

J. Michael Conlon, "Molecular Diversity, Localization, and Biological Actions of Elasmobranch Tachykinins", Journal of Experimental Zoology, 1999, pp. 535-540, vol. 284, XP008032621.
Ulf Norinder et al., "A Quantitative Structure-Activity Relationship Study of Some Substance P-Related Peptides", Journal of Peptide Research, 1997, pp. 155-162, vol. 49, Munksgaard International Publishers, ISSN: 1397-002X, XP000679593.
Yasuyuki Shimohigashi et al., "Discriminative Affinity Labeling of Tachykinin NK-1 and Nk-3 Receptors", Peptide Chemistry, 1993, pp. 337-340, XP1098649.
Iwakoshi E. et al., "Isolation of two novel tachykinins from the posterior salivary gland of Octopus Vulgaris," Zoological Science (Tokyo) (Dec. 1999), vol. 16, Suppl. p. 103.
Iwakoshi E. et al., "Cardioactive peptides isolated from the brain of Japanese octopus, Octopus minor," Peptides (May 2000), vol. 21, No. 5, pp. 623-630.
Martin R. et al., "The neurosecretory system of the octopus vena cava: (A) neurohemal organ," Experientia (1987), vol. 43, No. 5, pp. 537-543.
Champagne D. E. et al., "Sialokinin I and II: Vasodialatory tachykinins from the yellow fever mosquito aedes aegypti," Proc. Natl. Acad. Sci. USA (1994), vol. 91, No. 1.
International Search Report.

\* cited by examiner

*Primary Examiner*—Richard Hutson
*Assistant Examiner*—Jae Wan Lee
(74) *Attorney, Agent, or Firm*—Crowell & Moring LLP

(57) ABSTRACT

Tachykinin peptide isolated and purified from the posterior salivary gland of the mollusk *Octopus vulgaris*. The tachykinin peptide provides a new approach for developing medicaments and pesticides through studies on the structural activity correlation at the molecular level, is characterized by:
(1) number of amino acid residues is 12;
(2) N terminal of the peptide is Lys;
(3) an amino acid sequence of 5 amino acids from C-terminal is represented by the following amino acid sequence: Phe-Xaa-Gly-Leu-Met (SEQ ID NO: 6),
(wherein, Xaa is Val, lie, Phe or Tyr), especially following amino acid sequences are provided:
Lys-Pro-Pro-Ser-Ser-Ser-Glu-Phe-Val-Gly-Leu-Met (SEQ ID NO: 1),
Lys-Pro-Pro-Ser-Ser-Ser-Glu-Phe-Ile-Gly-Leu-Met (SEQ ID NO: 2).

6 Claims, 5 Drawing Sheets

Compound (1)

Compound (2)

$10^{-8}$M Compound (1)

$10^{-8}$M Compound (2)

FIG. 7

```
acagatctca caaaatttga gaagaaaatt ctataaaacc tgagaaatcc ctaatattcc   60
atacagattc ttattgtgat ttctatattc aac atg att aga gta ggt ttg atc  114
                                    Met Ile Arg Val Gly Leu Ile
                                     1               5 ctg tgt tgt atc ttc att gct gga gtg ttt gaa gcc agt tct gct gat  162
Leu Cys Cys Ile Phe Ile Ala Gly Val Phe Glu Ala Ser Ser Ala Asp
         10              15                  20 gac atg ctt aca gca cat aat ttg att aaa aga tct gaa gtt aaa cct  210
Asp Met Leu Thr Ala His Asn Leu Ile Lys Arg Ser Glu Val Lys Pro
     25                  30                  35 cct tca tcc tca gaa ttc ata ggc tta atg gga cgt tct gaa gag ttg  258
Pro Ser Ser Ser Glu Phe Ile Gly Leu Met Gly Arg Ser Glu Glu Leu
 40              45                  50                      55 aca cga cga tta att caa cat cct ggt tct atg tct gaa aca agt aag  306
Thr Arg Arg Leu Ile Gln His Pro Gly Ser Met Ser Glu Thr Ser Lys
                 60                  65                  70 aga ggt cca ccg aaa aaa gtt tct cgt cgt cca tat att ctt aag aaa  354
Arg Gly Pro Pro Lys Lys Val Ser Arg Arg Pro Tyr Ile Leu Lys Lys
             75                  80                  85 tgaatgttac caaaatattt caggcgattt taatcccaat gaactgaaac ctgaatctaa  414
catttgttaa aataaaatat gaaagcacaa aaaaaaaaaa aaaaaa                 460
```

US 7,371,810 B1

TACHYKININ PEPTIDES, PRECURSOR PEPTIDES THEREOF AND GENES ENCODING THE SAME

TECHNICAL FIELD

The present invention relates to novel tachykinin peptides having constricting activity for an intestine of a vertebrate animal, and precursor polypeptides thereof. More specifically, the present invention relates to novel tachykinin peptides, which have constricting activity for an intestine of the vertebrate animal, obtained from the posterior salivary gland of *Octopus vulgaris*, the precursor polypeptides thereof, and a gene encoding said polypeptides.

BACKGROUND ART

Eledoisin, which is isolated from an acetone extract of the posterior gland of the ocean *Eledone moschata* and *E. aldrovandi* and having a strong antihypertensive activity against a dog, is a physiologically active neuropeptide consisting of 11 amino acid residues (Erspamer, V., et al., *Experientia*, 18, 58, 1962). It has been obvious that the eledoisin shows a constricting activity of the ileum of a guinea pig other than an antihypertensive activity and also shows a specific action such as acceleration of salivary secretion of dog administered by intravenous injection.

Thereafter, the peptide having the same activities has been isolated from a skin of frog and this has been named physalaemin (Erspamer, V., et al. *Experientia*, 20, 489, 1964).

Such peptides were named tachykinin (tachy(=fast)kinin, something to contract quickly) against bradykinin (brady (=gradually)kinin, something to move gradually) because they have constricting activity against the ileum of a guinea pig quickly. Further, the chemical structure of substance P has been clarified based on the chemical structure of such peptides.

Though peptides classified into the tachykinin have been isolated thereafter one after another from the Amphibian class (Yasuhara, T., et al., *Biomed. Res.*, 2, 613, 1981) and the Avian class (Conlon, J. M., et al., *Regulatory Peptides*, 20, 171, 1988), sialokinin only has been found out from a mosquito which has mediated yellow fever other than eledoisin from a invertebrate animal (Champagne, D. E. & Ribeiro. J. M.: *Proc. Natl. Acad. Sci., USA*, 91, 138, 1994).

At present, tachykinin has a common amino acid sequence represented by the following formula in the C-terminal of a peptide:

Phe-Xaa-Gly-Leu-Met-$NH_2$ (SEQ ID NO: 6)

wherein, Xaa is aromatic amino acid (e.g., Phe, Tyr) and branched amino acid (e.g., Val, Ile). Tachykinin is used herein as a generic term of a physiologically active peptide indicating an intestine constricting activity, a hypotensive activity, a saliva secretion accelerating activity and the like. In such kinds of tachykinin, there are included aforementioned substance P, eledoisin, physalamine, neurokinin A, neurokinin B, kassinin and the like (SEIBUTUGAKU-JITEN (Ver. 4). Iwanami Shoten, 1997).

In this way, it has been expected to employ the tachykinin peptide as a basic chemical compound for developing a new medicine. In particular, since it has been considered that substance P has taken part in transmitting a pain as a transmitting substance of a primary sensory nerve, it has been expected and researched to develop as analgesics. Further, it has been expected to use practically a chemical reagent for elucidating an information processing mechanism in a nerve system of higher animals.

By the way, it is said that the posterior salivary gland of octopuses are venom gland since some of the salivary gland may include toxic substances such as tetrodotoxin known as fugu poison, and cephalotoxin that is a glycoprotein having an effect of numbing Crustaceans other than aforementioned eledoisin. Further, it has been known that they might include a biogenic amine group such as octopamine, serotonin, tyramine, noradrenaline, histamine, and acetylcholine and they might include an enzymatic group such as a proteolytic enzyme and hyaluronidase (Boucaud-Camou, E. & Boucher-Rodoni, R. 1983. Feeding and digestion in Cephalopods. In "*The mollusca*", (Saleuddin, A. S. M. & Wilbur, K. M.), Academic press and New York). It, however, has not been reported that the tachykinin peptide other than eledoisin has been found. Further, though it has been discovered that eledoisin shows smooth muscle constricting activity, angiectatic activity, and antihypertensive activity to the mammals, it has not been discovered that eledoisin has a role to the octopus.

In this way, it is required to find out the tachykinin peptides from greater number of animal species, in order to obtain information which is useful for development of the medicines and for solving an information processing mechanism in a nerve system of higher animals based on research and the like of a structure-activity relationship by elucidating a species specificity of the peptides and a role of each of animal species about the tachykinin peptides.

Therefore, the object of the present invention is to provide the novel tachykinin peptide capable of being used as a chemical reagent for elucidating an information processing mechanism in a nerve system of higher animals and as a basic chemical compound in developing the medicines and the pesticides by finding out the novel tachykinin peptides, making clear the structure thereof, and further elucidating the physiologically activities thereof.

Further, the object of the present invention is to provide a method for producing the tachykinin peptide by identifying the precursor polypeptide of such tachykinin peptide and gene encoding thereof.

DISCLOSURE OF THE INVENTION

To solve such problems, the present invention provides tachykinin peptide having following properties:

(1) the number of amino acid residues is 12;
(2) the N terminal of the peptide is Lys;
(3) an amino acid sequence of 5 amino acids from C-terminal is represented by the following amino acid sequence (I), Phe-Xaa-Gly-Leu-Met-$NH_2$ (SEQ ID NO: 6) (I), (wherein, Xaa is Val, Ile, Phe or Tyr).

Among them, the present invention provides a tachykinin peptide represented by the following amino acid sequence (II):

H-Lys-Pro-Pro-Ser-Ser-Ser-Glu-Phe-Xaa-Gly-Leu-Met-$NH_2$ (SEQ ID NO: 67) (II)

(wherein, Xaa is Val, Ile, Phe or Tyr).

In the present specification, as long as no condition is given, an amino acid residue is written by 3 letters notation defined by IUPAC and IUB.

That is, the present inventors performed the research for isolating the novel tachykinin peptide from a posterior salivary gland of *Octopus vulgaris* using the constricting activity of rectum of fishes (carps) as the parameter, among the aforementioned amino acid sequences (II), the peptides represented by the following amino acid sequences (1) and (2):

H-Lys-Pro-Pro-Ser-Ser-Ser-Glu-Phe-Val-Gly-Leu-Met-NH$_2$ (SEQ ID NO: 1) (1), (hereinafter, referred as Compound (1)), and H-Lys-Pro-Pro-Ser-Ser-Ser-Glu-Phe-Ile-Gly-Leu-Met-NH$_2$ (SEQ ID NO: 2) (2) (hereinafter, referred as Compound (2)) are isolated and purified, then identified chemical structures of these peptides and further confirmed the structure and physiological activities thereof by the total synthesis of these peptides.

Further, the present inventors determined the full primary amino acid sequence of polypeptides as a precursor of tachykinin peptides is represented by the amino acid SEQ ID NO: 4 by preparing the primers based on the aforementioned amino acid sequences and by combining analyzing methods of gene sequences using a reverse transcription polymerase chain reaction (RT-PCR) being performed to total RNA prepared from the posterior salivary gland of *Octopus vulgaris*.

The present inventors further determined the gene encoding the precursor polypeptide of the aforementioned tachykinin peptide has the base sequence represented by SEQ ID NO: 3.

Therefore, the present invention provides, as another embodiment, the precursor polypeptide of the tachykinin peptide represented by the amino acid SEQ ID NO: 4, or the amino acid sequence thereof partially modified by the addition or deletion of one or more than one amino acid, and/or the amino acid sequence thereof partially modified by the addition of another amino acid.

Furthermore, as another embodiment, the present invention provides a method for producing the gene encoding the aforementioned tachykinin peptide and precursor polypeptide, in particular, the gene consisting the base sequence represented by SEQ ID NO: 3, the tachykinin peptide and the precursor polypeptide by a gene recombinant technology using the gene or a host cell which is transformed by a vector and the vector including these genes.

BRIEF DESCRIPTION OF DRAWINGS

FIG. 7 shows the amino acid sequence of precursor polypeptide (SEQ ID NO: 3), in which the underlined part is the sequence of the amino acid of tachykinin peptide according to the present invention (SEQ ID NO: 7).

BEST MODE FOR CARRYING OUT THE INVENTION

Figure 1:
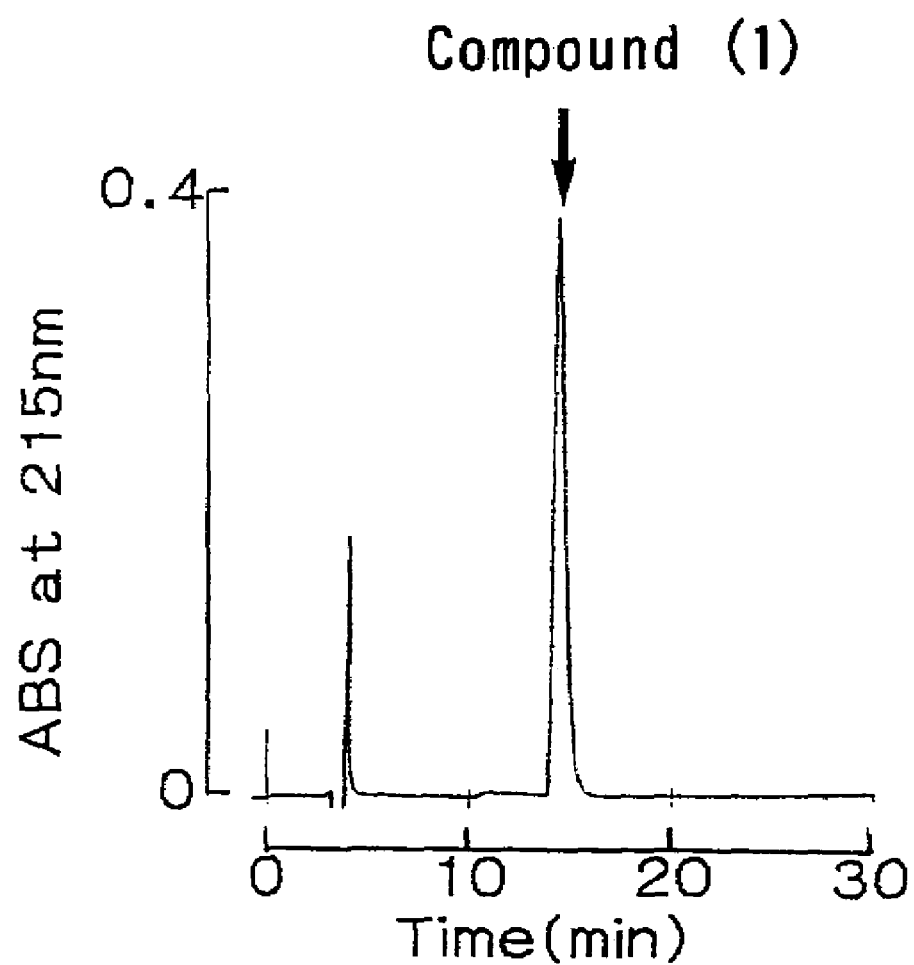
FIG. 1 shows the final eluted pattern of reversed-phase HPLC of Compound (1), a peptide of the present invention, in Example 2.

Novel peptide provided by the present invention is tachykinin peptide having constricting activity against an intestine of a vertebrate animal, and can be isolated and purified from *Octopus vulgaris* as follows.

For example, posterior salivary gland of *Octopus vulgaris* is extracted with hot water then acetic acid is added to the extract until it comes to be 3% concentration, and after cooling, a crude extract is obtained using a centrifuge separation method. After this crude extract is absorbed on C18 cartridge (e.g., Sep-Pak (Trade Mark) Cartridges: Waters Co.), a peptide containing fraction is eluted by using 60% methanol solution containing 0.1% trifluoro acetic acid (hereinafter referred as TFA) and then the purposed peptide can be separated and purified from the fraction by using an ion exchange chromatography, a reversed-phase chromatography, and the like.

Further, since the peptides of the present invention consist of 12 amino acid residues, they can be easily synthesized by the conventional solid phase method using the conventional peptide synthesizer (e.g., 433A peptide synthesizer, available from PE Bio Systems Japan) or the conventional organic synthetic method. The crude peptide obtained using such methods can be purified by way of the conventional purifying method such as the reversed-phase chromatography or a crystallizing method, if necessary.

Since the peptide of the present invention is the tachykinin peptide which causes a smooth muscle constricting activity, an angiectatic activity, and an antihypertensive activity, it may be used for the reagents for research on a neurotransmission system and further it provides the new approach for the development of drugs.

For example, the medicament containing the peptide of the present invention as active ingredient can be administered in the form of oral or parenteral formulations, such as capsules, tablets, or injectable solution, with excipient used commonly in the pharmaceutical field. More specifically, the peptide of the present invention can be mixed with excipient such as lactose, starch or derivative thereof, and cellulose derivatives, and the resulting mixture is filled into a gelatin capsule to obtain capsule formulation.

The tablet formulation can be prepared by kneading peptide together with the excipient mentioned above, binder such as sodium carboxymethyl cellulose, alginic acid and gum arabic, and water to prepare granule if necessary, and further lubricant such as talc, magnesium stearate, and then compressing by the conventional tableting machine.

For parenteral formulation, the injectable formulation containing the peptide of the present invention can be prepared by dissolving peptide with solubilizer in sterilized distilled water or in sterilized saline solution, and filled into ampule. The formulation may further contain stabilizer or buffer. The peptide of the present invention may be filled into vial in the powder form for in suite preparation with sterilized distilled water. These parenteral preparations may be administered by intravenous injection or drip.

The administration dose of the peptide of the present invention may vary in a wide range with ages, condition of patients, routes of administration or the like, and a usual recommended daily dose to adult patients for oral administration is within the range of approximately 0.1-1,000 mg/day/person, preferably 1-500 mg/day/person.

In the case of parenteral administration, a usual recommended daily dose is within the range of about 1/100 to 1/2 to the daily dose of oral administration.

EXAMPLE

The present invention will be described in detail with reference to the following examples; however, the present invention is not limited to the examples.

Example 1

Separation of Peptides having a Contractile Potentiating Activities Against a Carp Rectum from *Octopus vulgaris*

(a): Crude Extraction

The posterior salivary glands of 100 heads of *Octopus vulgaris* were excised and freezed under liquid nitrogen. The freezed tissues (221 g) were divided into 3 portions, and 1 portion thereof was boiled for 10 minutes in 800 ml of distilled water. After cooling, acetic acid was added to the solution until it has come to be 3% concentration, and the solution was homogenized and then supernatant fluid were collected by centrifugal separation for 30 minutes under 10,000×g at 4° C. The precipitate was added to 200 ml of 3% acetic acid/water solution, then homogenized and centrifuged again. This procedure was repeated. The remaining 2 portions of freezed tissues were treated with same procedure to obtain the supernatant fluid. All the extracts resulting from the above procedure were collected and concentrated to about 200 ml value under reduced pressure to give the crude extract.

(b): Adsorbing to C18 Cartridge

To the crude extract obtained in (a), was added 20 ml of 1.0 M HCl and the resulting mixture was centrifuged for 30 minutes at 4° C. under 30,000×g to obtain the supernatant. Thus obtained supernatant was pass through Sep-Pak (trade mark) Vac C18 cartridge (10 g, 35 cc, Waters Co.). After the cartridge was washed with 200 ml of 0.1% TFA, the maintained materials were eluted by 100 ml of 60% methanol/0.1% TFA solution, and the eluent was concentrated under reduced pressure, and the resulting residue was lyophilized to give 0.363 g of dried materials.

(C): Cation-Exchange Column Chromatography (1)

The dried materials obtained in (b) were dissolved in 150 ml of 10 mM phosphoric acid buffer solution (pH 7.0), and subjected to cation-exchange column chromatography using TSK-gel SP TOYOPERL PACK 650S (20 μm to 50 μm, 22Φ×200 mm, Tosoh Co.) with liner gradient from 0 to 0.6 M NaCl concentration (in 10 mM phosphoric acid buffer solution: pH 7.0) at a flow rate of the 3.0 ml/min over 60 minutes. 6 ml each of eluent, collected by monitoring UV absorbance at 215 nm and rectum contractile potentiating activity which was examined in accordance with the aftermentioned Example 6, was shown in the fraction eluting with 0 M NaCl concentration part.

(d): Reversed-phase high-performance liquid chromatography (HPLC) (1)

The active fractions obtained in (c) was subjected to the reversed-phase high-performance liquid chromatography (reversed-phase HPLC) using Capcell pak C18 UG80 (5 μm, 10Φ×250 mm, Shiseido Co.) with liner gradient from 0 to 60% acetonitrile (in 0.1% TFA/water: pH 2.2) at a flow rate 1.5 ml/min over 60 minutes. The fractions (3 ml each) eluted with 30 to 36% concentration of acetonitrile showed the constricting activity, and these fractions were collected.

(e): Cation-Exchange HPLC (2)

The obtained fraction in (d) was subjected cation-exchange HPLC using TSK-gel SP-5PW (10 μm, 7.5Φ×75 mm, Tosoh Co.) with linear gradient from 0 to 0.6 M NaCl concentration (in 10 mM phosphoric acid buffer solution: pH 4.7) at a flow rate of the 1.0 ml/min over 60 minutes. The fractions (2 ml each) eluted with 0.13 to 0.15 M NaCl concentration solution showed the constricting activity, and these fractions were collected.

(f): Reversed-Phase HPLC (2)

The fraction obtained in (e) was subjected to the reversed-phase HPLC using Capcell pak C18 UG80 (5 μm, 4.6Φ×150 mm, Shiseido Co.) with liner gradient from 20 to 40% acetonitrile (in 0.1% TFA/water: pH 2.2) at a flow rate 1.0 ml/min over 40 minutes.

The fraction (1 ml each) eluted with about 23% concentration of acetonitrile (hereinafter referred to as Fraction A), and the fraction eluted with about 25% concentration of acetonitrile (hereinafter referred to as Fraction B) showed the activity.

Example 2

Purification of a Peptides from an Active Fraction

No. 1: Purification from the Fraction A

The active Fraction A obtained by the separating operation (f) of Example 1 was subjected to the reversed-phase HPLC using Capcell pak C18 UG80 (5 μm, 4.6Φ×150 mm, Shiseido Co.) with 22% acetonitrile (in 0.1% TFA/water: pH 2.2) at a flow rate 0.5 ml/min. The compound shown a single peak at a retention time of 14.5 min was obtained, and this compound is defined as Compound (1).

The view of development of this reversed-phase HPLC is shown as FIG. 1.

Example 3

Purification of a Peptides from an Active Fraction

No. 2: Purification from the Fraction B

The active Fraction B obtained by the separating operation (f) of Example 1 was subjected to the reversed-phase HPLC using Capcell pak C18 UG80 (5 μm, 4.6Φ×150 mm, Shiseido Co.) with 24% acetonitrile (in 0.1% TFA/water: pH 2.2) at a flow rate 0.5 ml/min. The compound shown a single peak at a retention time of 13 min was obtained, and this compound is defined as Compound (2).

Figure 2:
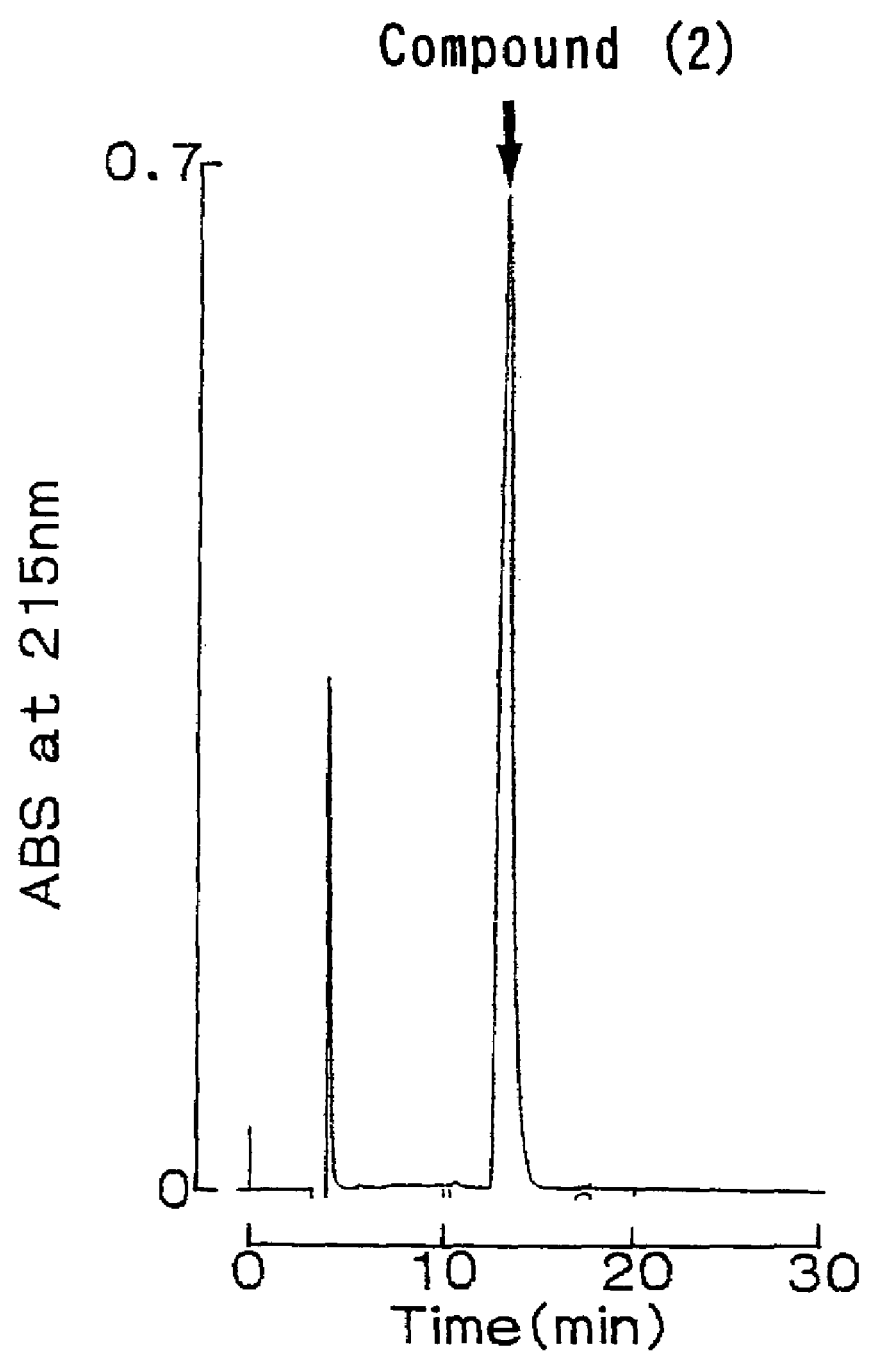
FIG. 2 shows the final eluted pattern of reversed-phase HPLC of Compound (2), a peptide of the present invention, in Example 3.

The view of development of this reversed-phase HPLC is shown as FIG. 2.

Example 4

Identification of the Peptides

The structures of the purified Compound (1) and (2) in the Example 2 and 3 were subjected to determination of the amino acid sequence using Shimadzu PSQ-1 type gaseous phase sequencer (Shimadzu Co.). The obtained amino acid sequences are shown in the following TABLE 1.

TABLE 1

Amino Acid Sequence of Peptides (unit: pmol)

| NO. | Compound (1) | | Compound (2) | |
|---|---|---|---|---|
| 1 | Lys | 103 | Lys | 114 |
| 2 | Pro | 121 | Pro | 137 |
| 3 | Pro | 104 | Pro | 124 |
| 4 | Ser | 22 | Ser | 30 |
| 5 | Ser | 18 | Ser | 26 |
| 6 | Ser | 14 | Ser | 14 |
| 7 | Glu | 64 | Glu | 48 |
| 8 | Phe | 27 | Phe | 22 |
| 9 | Val | 15 | Ile | 11 |
| 10 | Gly | 10 | Gly | 11 |
| 11 | Leu | 6 | Leu | 3 |
| 12 | Met | 2 | Met | 2 |

The molecular weights of Compound (1) and Compound (2) were determined by MALDI TOF-MS (Voyager Elite, PE Bio Systems Japan Co.).

The obtained molecular weights of the Compound (1) and (2) are shown in the following TABLE 2.

TABLE 2

Mass Date of Peptides

| Compound | Molecular formula | Calculated $(M + 2H)^{2+}$ | Found |
|---|---|---|---|
| (1) | $C_{57}H_{92}N_{14}O_{17}S$ | 639.31 | 639.37 |
| (2) | $C_{58}H_{94}N_{14}O_{17}S$ | 646.32 | 646.40 |

These results clearly show that the Compound (1), neuropeptide of *Octopus vulgaris*, isolated and purified from Fraction A is represented by the following amino acid sequence (SEQ ID NO: 1):

H-Lys-Pro-Pro-Ser-Ser-Ser-Glu-Phe-Val-Gly-Leu-Met-$NH_2$ (SEQ ID NO: 1).

Furthermore, the Compound (2), neuropeptide of Octopus vulgaris, isolated and purified from Fraction B is represented by the following amino acid sequence (2):

H-Lys-Pro-Pro-Ser-Ser-Ser-Glu-Phe-Ile-Gly-Leu-Met-$NH_2$ (SEQ ID NO: 2).

Example 5

Synthesis of peptides by solid phase method

Synthesis of peptides was performed by FastMoc (Trade Mark) solid phase method on an automatic 433A peptide synthesizer (PE Bio Systems Japan Co.). The Compound (1) was synthesized using Fmoc-NH-SAL-A resin (Watanabe Chemical Industries, Co.) as a support and Fmoc-Lys(Boc), Fmoc-Pro, Fmoc-Ser(tBu), Fmoc-Glu(OtBu), Fmoc-Phe, Fmoc-Val, Fmoc-Gly, Fmoc-Leu and Fmoc-Met.

Further, the Compound (2) was also synthesized using Fmoc-NH-SAL-A resin (Watanabe Chemical Industries, Co.) as a support and Fmoc-Lys(Boc), Fmoc-Pro, Fmoc-Ser (tBu), Fmoc-Glu(OtBu), Fmoc-Phe, Fmoc-Ile, Fmoc-Gly, Fmoc-Leu and Fmoc-Me.

(wherein, abbreviations used are as follows: Fmoc=9-Fluorenyl-methoxycarbonyl, Boc=t-Butoxycarbonyl, tBu=t-Butyl)

Procedures for cleavage of the each of the synthesized peptides from the peptide-resin conjugate and deprotection of the crude peptides were performed by using mixture solution of 4.3% of phenol/2.1% of 1,2-ethanedithiol/4.3% of thioanisole/4.3% of water/85% of TFA. The reaction mixtures were filtrated and the filtrate was washed with ether (3 times) to obtain about 100 mg of the crude peptides. About 10 mg of thus obtained 100 mg of crude peptide was subjected to reversed-phase HPLC to obtain about 6 mg of the purified peptide. The each resulting purified peptides thus obtained was identified with Compound (1) or Compound (2) of Octopus vulgaris by comparison with the same retention time in the reversed-phase HPLC using Capcell pak C18, respectively. Furthermore, the synthesized compounds and natural compounds have the same rectum constricting activities of the carp.

Example 6

Measurement of the Rectum Constricting Activity of the Carp

The rectum constricting activity of the carp was performed as follow. That is, the intestine of the carp was excised, and the both ends thereof were fastened with a cotton thread. Then, one end thereof was fixed to a sample chamber (2 ml capacity) and another end was fixed to a transducer to obtain a specimen for the examination. The samples to be measured were dissolved into the physiological saline solution, and added to the sample chamber. The changes of tension of the intestine by constriction were recorded. The results were shown in FIGS. 3 and 4.

Figure 3:
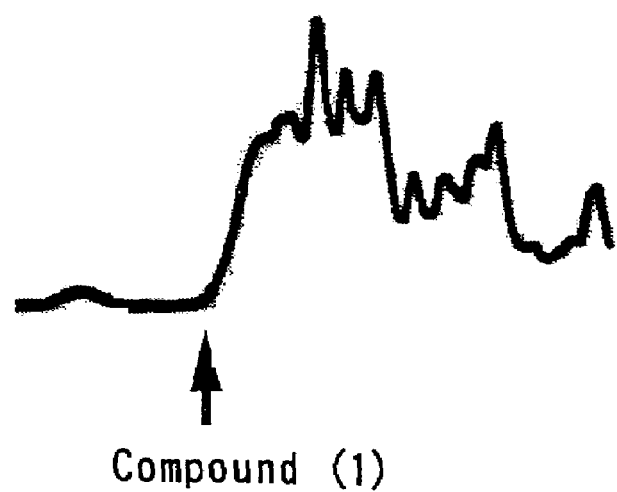
FIG. 3 shows the result of the constricting activity against the rectum of the carp by adding Compound (1) of the present invention to the chamber with the amount of corresponding to one head of *Octopus vulgaris*, in Example 6.
Figure 4:
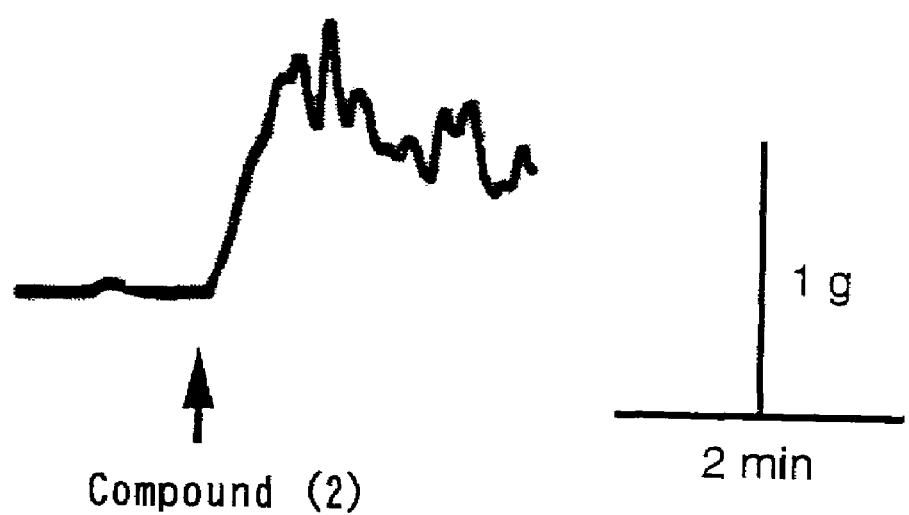
FIG. 4 shows the result of the constricting activity against the rectum of the carp by adding Compound (2) of the present invention to the chamber with the amount of corresponding one head of *Octopus vulgaris*, in Example 6.

As apparent from the results shown in the figures, by adding the Compound (1) [FIG. 3] and the Compound (2) [FIG. 4], the intestine of the carp was constricted strongly.

Example 7

Measurement of the Ileum Constricting Activity of the Guinea Pig

The ileum constricting activity of the guinea pig was performed in accordance with a method by Champagne et al. (Champagne D. E. et al., *Proc. Natl. Acad. Sci. USA.*, 91, 138-142, 1994).

The ileum of the guinea pig was excised, and the both ends thereof were fastened with a cotton thread. Then, one end thereof was fixed to a sample chamber (5 ml capacity) and another end was fixed to a transducer to obtain a specimen for the examination. The inside of the sample chamber was maintained constantly with 37° C. physiological saline. The samples to be measured were dissolved into the physiological saline solution, and added to the sample chamber. The changes of tension of the ileum by constriction were recorded. The results were shown in FIGS. 5 and 6.

Figure 5:
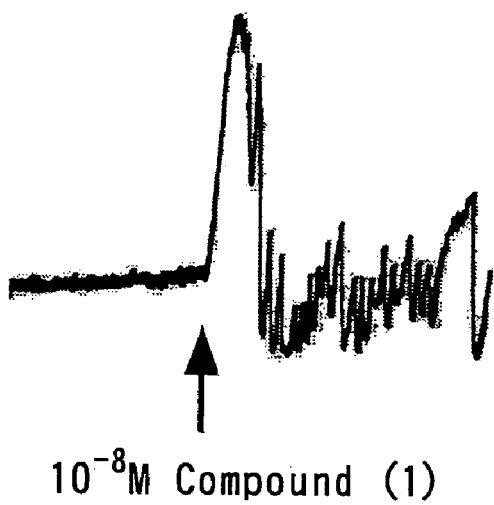
FIG. 5 shows the result of the constricting activity against the ileum of the guinea pig by adding Compound (1) of the present invention to the chamber with concentration of $1\times10^{-8}$M, in Example 7.
Figure 6:
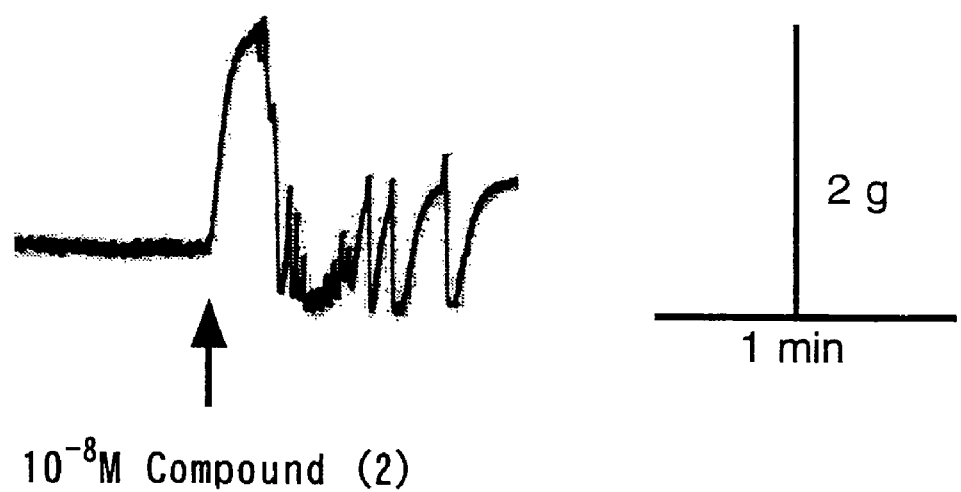
FIG. 6 shows the result of the constricting activity against the ileum of the guinea pig by adding Compound (2) of the present invention to the chamber with concentration of $1\times10^{-8}$M, in Example 7.

As apparent from the results shown in the figures, by adding the Compound (1) [FIG. 5] and the Compound (2) [FIG. 6], the ileum of the guinea pig was constricted strongly at the concentration of $1 \times 10^{-8}$ M of the compound.

Example 8

Determination of the Full Amino Acid Sequence of the Precursor Polypeptides and the Base Sequence of a Gene Encoding Thereof Preparation of Total RNA of the Posterior Salivary Gland of *Octopus vulgaris*

About 1 g of the posterior of salivary gland of Octopus vulgaris was crushed in the liquid nitrogen, and homogenized in 10 ml TRIzol (Trade Mark) reagent (GIBCO BRL Co.). After stably standing for 5 minutes at room temperature, divided into each 1 ml of the mixture. To this mixture was added 200 µl of chloroform, and the mixture was agitated, then centrifuged with the cooling centrifuge (Sakuma Co.) [15,000 rpm, for 15 minutes, at 4° C.]. After upper aqueous layer was fractionated, and to this solution was added 0.5 ml of isopropanol, the mixture was allowed to stand at room temperature for 10 minutes. The supernatant fluid was removed after the centrifugal separation (15,000 rpm, for 10 minutes, at 4° C.) using the cooling centrifuge, and then 1 ml of 75% ethanol was added to the residue. The supernatant fluid was removed after the centrifuge (10,00 rpm, for 5 minutes, at 4° C.) to obtain the residue, then, the air-drying of the residue was performed for about 10 minutes. 10 µl of DEPC-treated water was added to the resulting residue, and the mixture was incubated for 10 minutes at 60° C. to lyse RNA. About 3 mg of total RNA was obtained according to the above-mentioned methods.

Degenerate 3'-RACE

On the basis of amino acid sequence of the peptide isolated from posterior salivary gland of *Octopus vulgaris*, the following degenerate primers were designed and synthesized by the conventional method:

Oct-TK-M-1:

5'-AA(A/G)CCICCII(C/G)II(C/G)II(C/G)IGA(A/G)TT(C/T)AT-3' (SEQ ID NO: 8) Oct-TK-M

5'-GA(A/G)TT(C/T)AT(A/T/C)GGI(C/T)TIATGGG-3' (SEQ ID NO: 9):

(wherein, the above-mentioned alphabetic character was written based on the "Nucleotide Abbreviation List" (Cell Technology, separate volume, "*Biotechnology Experiment Illustrated*": Shunjunsha Co.); the same as the following each formulae)

Next, degenerate 3'-RACE was performed in accordance with the following steps using 5'/3'-RACE Kit (Boehringer Mannheim Co.). That is, 2 µg of total RNA, 4 µl of cDNA synthesis buffer, 2 µl of dNTP mix, 1 µl of oligo dT-anchor primer (12.5 pmol/µl) and 1 µl of AMV reverse transcriptase (20 units/µl) were added to the DEPC-treated water to obtain total volume of 20 µl, and the mixture was incubated for 60 minutes at 55° C., and then, the 1st-strand cDNA was synthesized by heating for 10 minutes at 65° C.

Next, 1st-3'-RACE was performed in the following conditions. That is, total 50 µl volume of the mixture solution of 5 µl of 1st-strand cDNA, 5 µl of 10×PCR buffer, 8 µl of dNTP mix, 3 µl of Oct-TK-M-1 (100 pmol/µl), 1 µl of PCR anchor primer (12.5 pmol/µl), 0.5 µl of TaKaRa Ex Taq (Trade Mark; Takara Shuzo Co.) and water was heated at 94° C. for 5 minutes, and was further heated for 30 cycles of 30 seconds at 94° C., 30 seconds at 45° C. and 2 minutes at 72° C. The reactant was then treated for 7 minutes at 72° C. For the polymerase chain reaction (PCR), GeneAmp PCR System 2400 thermal cycler (Perkin Elmer Co.) was used.

Subsequently, 1st-PCR product was purified by the spin column [MicroSpin (Trade Mark) S-400, Amersham Pharmacia Co.], and then 2nd-3'-RACE was performed in the following conditions. That is, total 50 µl of the mixture solution of 3 µl of 1st-PCR product, 5 µl of 10×PCR buffer, 8 µl of DNTP mix, 3 µl of Oct-TK-M (100 pmol/µl), 1 µl of PCR anchor primer (12.5 pmol/µl), 0.5 µl of TaKaRa Ex Taq [Trade Mark; Takara Shuzo Co.] and water was heated at 94° C. for 5 minutes, and was further heated for 30 cycles of 30 seconds at 94° C., 30 seconds at 45° C. and 2 minutes at 72° C. The reactant was then heated for 7 minutes at 72° C.

5 µl of the obtained reaction solution was electrophoresed on 1.5% agarose gel to confirm the amplified PCR products at the size of about 300 bp.

Ligation of PCR Product

The PCR product was purified on the spin column, and 3 µl of the PCR product was mixed with 2 µl of TA cloning vector pCR 2.1 (Invitrogene Co.) and 5 µl of Ligation high (Toyobo Co.), and then this mixture was subjected for ligation for 1 hour at 16° C.

Transformation of *Escherichia coli*

To the 10 µl of ligation reaction solution obtained in the aforementioned (3) was added competent cell, Competent high *E. coli* DH5α (Toyobo Co.), and the mixture was allowed to stand in the ice bath for 30 minutes. Then, the mixture was subjected for heat shocking for 50 seconds at 42° C. After cooling for 2 minutes in ice bath, 1 ml of SOC medium was added to the mixture and the mixture was incubated for 30 minutes at 37° C. Subsequently, 10 µl of the transforming solution was spread on LB/Amp. agar culture (LB agar culture containing 50 µg/ml of ampicillin), which is coated with 35 µl of X-gal. The residual transforming solution was centrifuged under 10,000 rpm for 1 minute to decrease the volume of about 100 µl, and the whole volume thereof was spread on LB/Amp. agar culture. The LB/Amp. agar culture was incubated over night at 37° C.

Colony PCR

The colony PCR was performed under the following conditions using the colony obtained above as a template. Namely, total 50 µl volume of the mixture solution of the strain of *Escherichia coli* 5 µl of 10× reaction buffer, 5 µl of 2 mM dNTPs, 3 µl of 25 mM $MgCl_2$, 0.5 µl of M13FW primer (100 pmol/µl), 0.5 µl of M13RV primer (100 pmol/µl), 0.5 µl of rTaq DNA polymerase (Toyobo Co.) and water was heated at 94° C. for 10 minutes, and was further heated for 30 cycles of 30 seconds at 94° C., 30 seconds at 55° C. and 1 minute at 72° C. The reactant was then heated for 5 minutes at 72° C. Then, 5 µl of the obtained reaction solution was electrophoresed on 1.5% agarose gel.

The M13FW primer and M13RV primer used in this reaction were synthesized using the conventional method, and the sequences thereof are indicated in the following:

M13FW: 5'-GTAAAACGACGGCCAGTG-3' (SEQ ID NO: 10), and

M13RW: 5'-GGAAACAGCTATGACCATG-3' (SEQ ID NO: 11).

DNA Sequence

The colony PCR product having the targeted size (about 500 bp) was purified on the spin column, and the sequencing of the obtained product was conducted by using DNA Sequencing Kit (PE Biosystems Co.). For the sequencing, ABIPRISM 310 Genetic Analyzer (PE Biosystems Co.) was used.

The obtained sequence was analyzed using gene analysis software GENETYX-MAC (Software Development Co.). As the result, the partial cDNA of about 500 bp was analyzed.

5'-RACE

The following primers were synthesized based on the base sequences of the partial cDNA.

TK-M-5'-1R: 5'-TTCAGGTTTCAGTTCATTGGG-3' (SEQ ID NO: 12)

TK-M-5'-2R: 5'-TTTCGGTGGACCTCTCTTAC-3' (SEQ ID NO: 13)

TK-M-5'-3R: 5'-TTCAGACATAGAACCAGGATG-3' (SEQ ID NO: 14).

Next, according to the following procedure, 5'-RACE was performed using 5'/3'-RACE Kit (Boehringer Mannheim Co.). Firstly, 2 μg of total RNA and 1 μl of TK-M-5'-1R (12.5 pmol/μl) were mixed, and the mixture was incubated for 10 minutes at 70° C., and then, cooled in the ice bath. To this mixture was added 4 μl of cDNA synthesis buffer, 2 μl of dNTP mix, 1 μl of AMV reverse transcriptase (20 units/l), DEPC-treated water to obtain the total volume of 20 μl, and the mixture was incubated for 60 minutes at 55° C. and for 10 minutes at 65° C. to obtain 1st-strand cDNA. Next, 1st-strand cDNA thus obtained was purified on the spin column, then, 2.5 μl of reaction buffer and 2.5 μl of 2 mM DATP were added to the 1st-strand cDNA, and the mixture was allowed to stand 3 minutes at 94° C. Terminal transferase (10 units/μl) was added to the mixture, and the resulting mixture was incubated for 20 minutes at 37° C., and for 10 minutes at 70° C. to obtain da-tailed cDNA.

Next, 1st-PCR and 2nd-PCR were performed under the following conditions:

① 1st-PCR

Total 50 μl volume of the mixture solution of 5 μl of dA-tailed cDNA, 5 μl of 10×PCR buffer, 8 μl of DNTP mix, 1 μl of TK-M-5'-2R (12.5 pmol/μl), 1 μl of oligo dT-anchor primer (12.5 pmol/μl), 0.5 μl of TaKaRa Ex Taq [Trade Mark: Takara Shuzo Co.] and water was heated at 94° C. for 5 minutes, and was further heated for 30 cycles of 30 seconds at 94° C., 30 seconds at 55° C. and 2 minutes at 72° C. The reactant was then heated for 7 minutes at 72° C.

② 2nd-PCR:

Total 50 μl volume of the mixture solution of 3 μl of 1st-PCR product purified on the spin column, 5 μl of 10×PCR buffer, 8 μl of dNTP mix, 1 μl of TK-M-5'-3R (12.5 pmol/μl), 1 μl of PCR anchor primer (12.5 pmol/μl), 0.5 μl of TaKaRa Ex Taq [Trade Mark: Takara Shuzo Co.] and water was heated by the same procedure as described in 1st-PCR above.

The obtained 2nd-PCR product was electrophoresed on 1.5% agarose gel to confirm the band about 300 bp.

This 2nd-PCR product was sequenced in accordance with the methods described in aforementioned (3), (4), (5), and (6), respectively.

As a result, the size (about 460 bp), the sequence and the number (about 87 amino acid residues) of cDNA encoding the precursor polypeptides of tachykinin peptides of the present invention become clear. The amino acid sequence is represented by SEQ ID NO: 4, and the sequence of cDNA is represented by SEQ ID NO: 3.

Furthermore, among the precursor polypeptides, the parts in which the amino acid sequence corresponding to the tachykinin peptides of the present invention is shown in FIG. 7. In the figure, the underlined part is the sequence of the amino acid of the peptides according to the present invention.

Example 9

Formulation Examples

| Tablets: | |
|---|---|
| Components: Compound (1) or (2) | 10 g |
| Lactose | 125 g |
| Fine crystalline cellulose | 25 g |
| Corn starch | 25 g |
| 5% Hydroxypropyl methylcellulose | 100 ml |
| Magnesium stearate | 5 g |

The above components were mixed and kneaded. The resulting mixture was granulated, dried and then, tabletted to produce tablets weighting 190 mg each containing 10 mg of Compound (1) or (2).

INDUSTRIAL APPLICABILITY

The neuropeptide derived from Octopus vulgaris provided by the present invention is neuropeptide, which quickly constricts the rectum of a carp at the low concentration and continuously shows constricting activity to the rectum of the carp. These results are similar to the two phases' constricting activity against smooth muscle characterized by substance P.

Further, the neuropeptide derived from *Octopus vulgaris* provided by the present invention has an amino acid sequence in the C terminal of peptide represented by the following formula:

Phe-Xaa-Glv-Leu-Met-NH$_2$ (SEQ ID NO: 6)

(wherein, Xaa has the same meaning as mentioned above)

which is characteristic to the amino acid sequence of tachykinin peptide having constricting activity against smooth muscle, vasodilative activity, and antihypertensive activity in the mammals.

Therefore, the neuropeptides of Octopus vulgaris of the present invention are useful as a biochemical reagent for analyzing a neurotransmission system, and it provides the new approach directed to development of drugs, such as the medicine or pesticides on the basis of study of correlation of the structural activity in a molecular level.

Further, the precursor polypeptides of the tachykinin peptides and gene encoding thereof provided by the present invention come to be an important tool for manufacturing the tachykinin peptides of the present invention.

The invention claimed is:

1. An isolated tachykinin peptide consisting of SEQ ID NO: 7.

2. The peptide according to claim 1, wherein the peptide is obtained from posterior salivary gland of *Octopus vulgaris*.

3. The peptide according to claim 1, wherein the peptide consists of SEQ ID NO: 1.

4. The peptide according to claim 1, wherein the peptide consists of SEQ ID NO: 2.

5. An isolated precursor polypeptide of tachykinin peptide having the amino acid sequence consisting of SEQ ID NO: 4, wherein the tachykinin peptide obtained from the precursor consists of SEQ ID NO: 7.

6. A medicament or pesticide comprising the tachykinin peptide according to claim 1.

* * * * *

SEQUENCE LISTING

<160> NUMBER OF SEQ ID NOS: 14

<210> SEQ ID NO 1
<211> LENGTH: 12
<212> TYPE: PRT
<213> ORGANISM: OCTOPUS VULGARIS

<400> SEQUENCE: 1

Lys Pro Pro Ser Ser Glu Phe Val Gly Leu Met
1               5                   10

<210> SEQ ID NO 2
<211> LENGTH: 12
<212> TYPE: PRT
<213> ORGANISM: OCTOPUS VULGARIS

<400> SEQUENCE: 2

Lys Pro Pro Ser Ser Glu Phe Ile Gly Leu Met
1               5                   10

<210> SEQ ID NO 3
<211> LENGTH: 460
<212> TYPE: DNA
<213> ORGANISM: Octopus vulgaris
<220> FEATURE:
<221> NAME/KEY: CDS
<222> LOCATION: (94)..(354)
<223> OTHER INFORMATION:

<400> SEQUENCE: 3

```
acagatctca caaaatttga gaagaaaatt ctataaaacc tgagaaatcc ctaatattcc         60
atacagattc ttattgtgat ttctatattc aac atg att aga gta ggt ttg atc        114
                                    Met Ile Arg Val Gly Leu Ile
                                    1               5 ctg tgt tgt atc ttc att gct gga gtg ttt gaa gcc agt tct gct gat         162
Leu Cys Cys Ile Phe Ile Ala Gly Val Phe Glu Ala Ser Ser Ala Asp
        10                  15                  20 gac atg ctt aca gca cat aat ttg att aaa aga tct gaa gtt aaa cct         210
Asp Met Leu Thr Ala His Asn Leu Ile Lys Arg Ser Glu Val Lys Pro
    25                  30                  35 cct tca tcc tca gaa ttc ata ggc tta atg gga cgt tct gaa gag ttg         258
Pro Ser Ser Ser Glu Phe Ile Gly Leu Met Gly Arg Ser Glu Glu Leu
40                  45                  50                  55 aca cga cga tta att caa cat cct ggt tct atg tct gaa aca agt aag         306
Thr Arg Arg Leu Ile Gln His Pro Gly Ser Met Ser Glu Thr Ser Lys
                60                  65                  70 aga ggt cca ccg aaa aaa gtt tct cgt cgt cca tat att ctt aag aaa         354
Arg Gly Pro Pro Lys Lys Val Ser Arg Arg Pro Tyr Ile Leu Lys Lys
            75                  80                  85 tgaatgttac caaatatttt caggcgattt taatcccaat gaactgaaac ctgaatctaa       414
catttgttaa aataaaatat gaaagcacaa aaaaaaaaaa aaaaaa                     460
```

<210> SEQ ID NO 4
<211> LENGTH: 87
<212> TYPE: PRT
<213> ORGANISM: Octopus vulgaris

<400> SEQUENCE: 4

Met Ile Arg Val Gly Leu Ile Leu Cys Cys Ile Phe Ile Ala Gly Val
1               5                   10                  15

Phe Glu Ala Ser Ser Ala Asp Asp Met Leu Thr Ala His Asn Leu Ile
            20                  25                  30

Lys Arg Ser Glu Val Lys Pro Pro Ser Ser Ser Glu Phe Ile Gly Leu
        35                  40                  45

Met Gly Arg Ser Glu Glu Leu Thr Arg Arg Leu Ile Gln His Pro Gly
    50                  55                  60

```
Ser Met Ser Glu Thr Ser Lys Arg Gly Pro Pro Lys Lys Val Ser Arg
 65                  70                  75                  80

Arg Pro Tyr Ile Leu Lys Lys
                85
```

<210> SEQ ID NO 5
<211> LENGTH: 87
<212> TYPE: PRT
<213> ORGANISM: OCTOPUS VULGARIS

<400> SEQUENCE: 5

```
Met Ile Arg Val Gly Leu Ile Leu Cys Cys Ile Phe Ile Ala Gly Val
 1               5                  10                  15

Phe Glu Ala Ser Ser Ala Asp Asp Met Leu Thr Ala His Asn Leu Ile
                20                  25                  30

Lys Arg Ser Glu Val Lys Pro Pro Ser Ser Ser Glu Phe Ile Gly Leu
                35                  40                  45

Met Gly Arg Ser Glu Glu Leu Thr Arg Arg Leu Ile Gln His Pro Gly
            50                  55                  60

Ser Met Ser Glu Thr Ser Lys Arg Gly Pro Pro Lys Lys Val Ser Arg
 65                  70                  75                  80

Arg Pro Tyr Ile Leu Lys Lys
                85
```

<210> SEQ ID NO 6
<211> LENGTH: 5
<212> TYPE: PRT
<213> ORGANISM: Unknown
<220> FEATURE:
<223> OTHER INFORMATION: The C terminal of tachychinin
<220> FEATURE:
<221> NAME/KEY: misc_feature
<222> LOCATION: (2)..(2)
<223> OTHER INFORMATION: Xaa is an aromatic (e.g. Phe or Tyr) or a
      branched amino acid (e.g. Val or Ile).
<220> FEATURE:
<221> NAME/KEY: misc_feature
<222> LOCATION: (2)..(2)
<223> OTHER INFORMATION: Xaa is an aromatic (e.g. Phe or Tyr) or a
      branched amino acid (e.g. Val or Ile)

<400> SEQUENCE: 6

```
Phe Xaa Gly Leu Met
 1               5
```

<210> SEQ ID NO 7
<211> LENGTH: 12
<212> TYPE: PRT
<213> ORGANISM: Unknown
<220> FEATURE:
<223> OTHER INFORMATION: artificially modified partial sequence of
      tachychinin
<220> FEATURE:
<221> NAME/KEY: misc_feature
<222> LOCATION: (9)..(9)
<223> OTHER INFORMATION: X is Phe, Tyr, Val, or Ile

<400> SEQUENCE: 7

```
Lys Pro Pro Ser Ser Ser Glu Phe Xaa Gly Leu Met
 1               5                  10
```

<210> SEQ ID NO 8
<211> LENGTH: 26
<212> TYPE: DNA
<213> ORGANISM: Unknown
<220> FEATURE:

<223> OTHER INFORMATION: artificially modified partial sequence of
      tachychinin
<220> FEATURE:
<221> NAME/KEY: misc_feature
<222> LOCATION: (6)..(6)
<223> OTHER INFORMATION: n is I (inosine)
<220> FEATURE:
<221> NAME/KEY: misc_feature
<222> LOCATION: (6)..(6)
<223> OTHER INFORMATION: n is I (inosine)
<220> FEATURE:
<221> NAME/KEY: misc_feature
<222> LOCATION: (9)..(10)
<223> OTHER INFORMATION: n is I (inosine)
<220> FEATURE:
<221> NAME/KEY: misc_feature
<222> LOCATION: (12)..(13)
<223> OTHER INFORMATION: n is I (inosine)
<220> FEATURE:
<221> NAME/KEY: misc_feature
<222> LOCATION: (15)..(16)
<223> OTHER INFORMATION: n is I (inosine)
<220> FEATURE:
<221> NAME/KEY: misc_feature
<222> LOCATION: (18)..(18)
<223> OTHER INFORMATION: n is I (inosine)

<400> SEQUENCE: 8
aarccnccnn snnsnnsnga rttyat                                      26

<210> SEQ ID NO 9
<211> LENGTH: 20
<212> TYPE: DNA
<213> ORGANISM: Unknown
<220> FEATURE:
<223> OTHER INFORMATION: artificially modified partial sequence of
      tachychinin
<220> FEATURE:
<221> NAME/KEY: misc_feature
<222> LOCATION: (12)..(12)
<223> OTHER INFORMATION: n is I (inosine)
<220> FEATURE:
<221> NAME/KEY: misc_feature
<222> LOCATION: (15)..(15)
<223> OTHER INFORMATION: n is I (inosine)

<400> SEQUENCE: 9
garttsathg gnstnatggg                                             20

<210> SEQ ID NO 10
<211> LENGTH: 18
<212> TYPE: DNA
<213> ORGANISM: Unknown
<220> FEATURE:
<223> OTHER INFORMATION: oligonucleotide primer

<400> SEQUENCE: 10
gtaaaacgac ggccagtg                                               18

<210> SEQ ID NO 11
<211> LENGTH: 19
<212> TYPE: DNA
<213> ORGANISM: Unknown
<220> FEATURE:
<223> OTHER INFORMATION: oligonucleotide primer

<400> SEQUENCE: 11
ggaaacagct atgaccatg                                              19

<210> SEQ ID NO 12
<211> LENGTH: 21

```
<212> TYPE: DNA
<213> ORGANISM: Unknown
<220> FEATURE:
<223> OTHER INFORMATION: oligonucleotide primer

<400> SEQUENCE: 12
ttcaggtttc agttcattgg g                                          21

<210> SEQ ID NO 13
<211> LENGTH: 20
<212> TYPE: DNA
<213> ORGANISM: Unknown
<220> FEATURE:
<223> OTHER INFORMATION: oligonucleotide primer

<400> SEQUENCE: 13
tttcggtgga cctctcttac                                            20

<210> SEQ ID NO 14
<211> LENGTH: 21
<212> TYPE: DNA
<213> ORGANISM: Unknown
<220> FEATURE:
<223> OTHER INFORMATION: oligonucleotide primer

<400> SEQUENCE: 14
ttcagacata gaaccaggat g                                          21
```